March 11, 1952 L. GHIO Plant Pat. 1,077
SAINTPAULIA OR AFRICAN VIOLET PLANT
Filed July 5, 1949
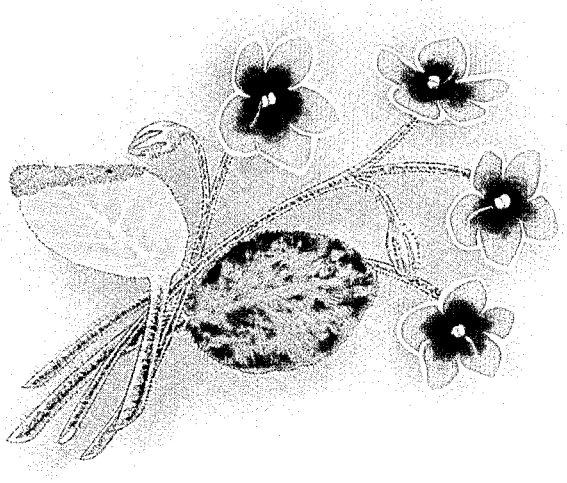
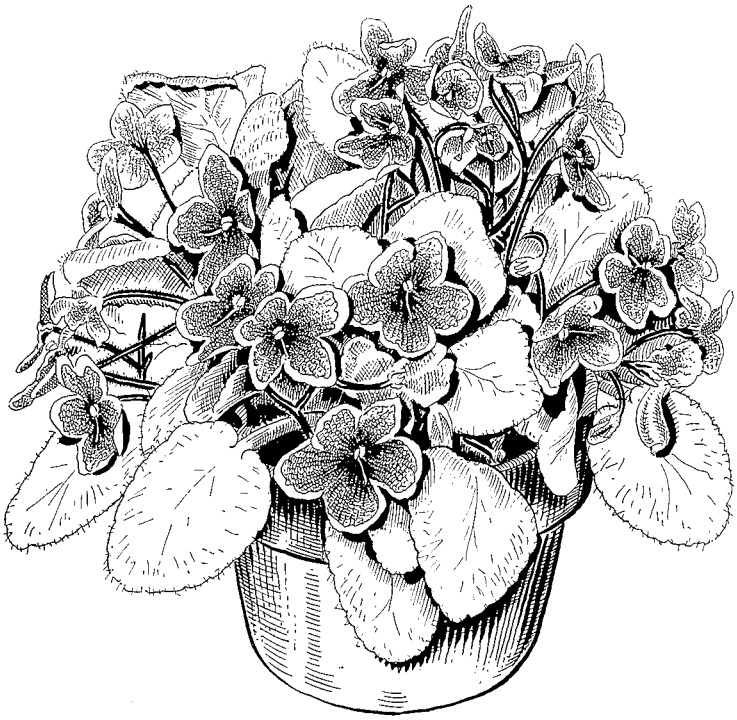
INVENTOR.
Louis Ghio
BY
M. S. Graham Patented Mar. 11, 1952

Plant Pat. 1,077

UNITED STATES PATENT OFFICE 1,077

SAINTPAULIA OR AFRICAN VIOLET PLANT

Louis Ghio, San Francisco, Calif.

Application July 5, 1949, Serial No. 103,141

1 Claim. (Cl. 47—60)

This invention and discovery relates to a distinct and new variety of plant of the species known botanically as Saintpaulia and generally known as African violet. Although African violets produce blooms of various colors, such as white, pink and blue, and possibly others, this invention and discovery relates to the species in which the blooms have the characteristic of a violet shade of blue color.

The new variety of African violet plant and its distinctive characteristic is illustrated in the accompanying illustration in color, the colors being specifically described in tabular form herein according to "A Dictionary of Color" by Maerz and Paul.

This new variety is particularly and distinctly characterized, in that each of the five lobate petals of the bloom of this new variety has a white peripheral edge portion approximately one thirty-second ($\frac{1}{32}$) of an inch in width extending around the entire peripheral edge portion of each of the lobes or petals of the violet-blue bloom. The other characteristics of this new variety are well known in previously existing African violet plants of the type having violet-blue blooms.

The new and distinct variety was originated and discovered as a bud sport of a plant of well known violet-blue African violet, in a glass house under my supervision and control in San Francisco, California, and in an immediate environment of several thousand of other plants of African violets having the well-known characteristic of violet-blue color of the petals of the bloom.

It was noted that one plant centrally situated with relation to other African violet plants of the type having violet-blue petals to the blooms, had blooms on approximately one-half of the plant which were of the characteristic well-known violet-blue color throughout the area of the lobes or petals of the bloom, whereas the blooms on the other approximate half of the plant had violet-blue blooms in which the individual lobes or petals had a white edging about one thirty-second ($\frac{1}{32}$) of an inch wide at the peripheral edge of each of the five lobes of the bloom.

This one plant was of parentage similar to all the other African violet plants having violet-blue blooms, which were in the same immediate environment.

This one plant having the sport of new variety was removed from its immediately surrounding plants and placed separately in the glass house, carefully protected from direct rays of the sun as is usual in growing African violets, and was treated, watered and nurtured similar to other plants of the African violet species. It developed no other distinctive characteristics not common to African violets of the characteristic violet-blue color.

The parent plant having the sport of new variety had eight leaves. All of the eight leaves were planted as leaf cuttings in separate pots and treated to similar growing conditions in the same glass house. Three of the leaf cuttings produced plants which had the ordinary violet-blue hue and color throughout the petals of the bloom. Five of the leaf cuttings produced plants all the blooms of which had petals including the distinct characteristic of white peripheral edge portion of the petals as previously described. From these five plants the plant of the new variety has been successively reproduced asexually, by leaf cuttings. Its asexual reproduction has been uniform in character and detail with customary propagation of other plants of African violets.

The asexual reproduction of the new variety having aforesaid distinctive characteristic has been thoroughly established and fixed through asexual propagation in like manner of leaf cuttings through at least five generations of asexual propagation in the same glass house at San Francisco, California, through a period of two years.

The following is a detailed description of this new variety:

*Parentage*

Origin: Bud sport.

Parentage:

*Parent variety.*—Saintpaulia or African violet of violet-blue bloom variety.

*Flower*

Blooming habit: Recurrent and continual.

Bud:

*Size.*—⅛ to ¼ inch, ball form.

*Balled petals.*—Color—pinkish blue.

*Calyx.*—Color—greenish red; form—gamosepalous; sepals, usually 5 acuminate.

Bloom:

*Size.*—¾ to 1¼ inch between opposite tips of lobes.

*Form.*—Short tubed, gamopetalous corolla, 5 ovate lobes.

*Borne.*—Clusters of 3 to 5, cymose.

*Stems.*—Slender, length 1 to 1¼ inch; peduncles, length 2 to 3 inches from cyme to base; color of stems and peduncles brownish red.

*Petalage.*—Gamopetalous; number, 5 lobes; color, violet shade of blue, except that each lobe has a substantially white peripheral edge strip about $\frac{1}{32}$ inch in width.

*Fragrance.*—None.

*Persistence of bloom.*—Deciduous; lasting quality, good, petals hold to bloom (average) 10 days.

*Texture.*—Silky obverse surface.

Genital organs:

*Stamens.*—Color, whitish green; number, 2; length ⅜ inch.

*Anthers.*—Color, yellow, closely side by side in abutting pairs.

*Pollen.*—Color, yellow.

*Style.*—Color, violet blue; 1 in number; length short (average) ¾ inch.

*Stigma.*—Inconspicuous, very small.

*Ovary.*—Single with plural ovules.

*Plant (other than inflorescence)*

Form:

*Size.*—Overall diameter 6 to 9 inches; height 5 to 6 inches; structure—overlapping rosette growth of foliage leaves erect at center of plant and inclined outwardly horizontally planar at perimeter of plant.

Foliage leaves:

*Shape.*—Prolately ovate-cordate, slightly scalloped convexly at peripheral edge.

*Color.*—Upper or obverse face, green; lower or reverse face, light green.

*Size of leaves.*—Axially 2 to 2½ inches; transversely 1½ to 2 inches.

*Texture.*—Subcoreaceous, pubescent.

*Petioles.*—Color, pink; length 2 to 3 inches; erect at center and inclined outwardly at perimeter of plant. Pinkish color of petioles extends into midrib and major venation of some, but not all, of foliage leaves.

*Asexual reproduction*

By leaf cuttings.

The color designations according to "A Dictionary of Color" by Maerz and Paul, are as follows:

| Part of Plant | Color | Plate | Column Letter | Line No. |
|---|---|---|---|---|
| Parent Variety: | | | | |
| Bloom, petalage | Violet-blue | 41 | L | 11 |
| This New Variety— | | | | |
| Bud: | | | | |
| Balled petals | Pinkish-blue | 44 | L | 8 |
| Calyx | Greenish-red | 55 | H | 5 |
| Bloom: | | | | |
| Stems and peduncles. | Brownish-red | 55 | J | 5 |
| Petalage | Violet-blue | 41 | L | 11 |
| Edge strip of petal lobes. | White | 41 | A | 2 |
| Genital Organs: | | | | |
| Stamens | Whitish-green | 17 | B | 2 |
| Anthers | Yellow | 17 | L | 1 |
| Pollen | do | 17 | L | 1 |
| Style | Violet-Blue | 41 | L | 11 |
| Foliage Leaves: | | | | |
| Obverse face | Green | 22 | L | 8 |
| Reverse face | Light green | 17 | B | 2 |
| Petioles | Pinkish | 53 | J | 4 |

I claim:

A new and distinct variety of African violet plant, substantially as described and illustrated, having blooms the petals of which have violet-blue color with a white edge portion substantially one thirty-second of an inch in width around the peripheral edge portion of the petals.

LOUIS GHIO.

REFERENCES CITED

The following references are of record in the file of this patent:

UNITED STATES PATENTS

| Number | Name | Date |
|---|---|---|
| Pl. Pt. 535 | Ulery | July 28, 1942 |
| Pl. Pt. 769 | Baxter | Dec. 16, 1947 |
| Pl. Pt. 770 | Baxter | Dec. 16, 1947 |